United States Patent [19]

Pallos

[11] Patent Number: 4,468,246
[45] Date of Patent: Aug. 28, 1984

[54] GUANIDINYL HERBICIDE ANTIDOTES

[75] Inventor: Ferenc M. Pallos, Walnut Creek, Calif.

[73] Assignee: Stauffer Chemical Company, Westport, Conn.

[21] Appl. No.: 356,669

[22] Filed: Mar. 10, 1982

[51] Int. Cl.³ .......................................... A01N 25/32
[52] U.S. Cl. ........................................ 71/100; 71/121
[58] Field of Search ................................... 71/100, 121

[56] References Cited
PUBLICATIONS

Golyshin et al., Chem. Abst., vol. 79, (1973) 66052f.

*Primary Examiner*—Catherine L. Mills
*Attorney, Agent, or Firm*—Harry A. Pacini

[57] ABSTRACT

Herbicide antidote compounds and herbicidal compositions according consisting of an active herbicide compound and an antidote therefore and the methods of use of the antidote compound and compositions wherein the antidote compounds correspond to the formula

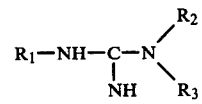

wherein $R_1$ is halo substituted phenyl, $R_2$ and $R_3$ are individually selected from alkyl $C_1$–$C_4$ and alkenyl $C_3$–$C_4$.

12 Claims, No Drawings

GUANIDINYL HERBICIDE ANTIDOTES

BACKGROUND OF THE INVENTION

While many herbicides are immediately toxic to a large number of weed pests, it is known that the effect of many herbicides upon important plant cultivations is either non-selective or not adequately selective. Thus, many herbicides damage not only the weeds to be controlled, but to a greater or lesser extent, the desirable cultivated plants as well. This holds true for many herbicidal compounds which have been commercially successful and are commercially available. These herbicides include types such as triazines, phenylurea derivatives, halogenated acetanilides, carbamates, thiolcarbamates, thiolcarbamate sulfoxides, pyrrolidinones, benzonitriles, toluidine derivatives, and the like. Some examples of these compounds are described in U.S. Pat. Nos. 2,891,855, 2,913,237, 3,027,248, 3,037,853, 3,175,897, 3,185,720, 3,198,786, 3,257,190, 3,442,945, 3,582,314, 3,780,090, 3,952,056 and 4,110,105.

The side effect of injury to a cultivated crop by various herbicides is particularly inconvenient and unfortunate. When used in the recommended amounts in the soil to control broadleaf weeds and grasses, injury such as serious malformation or stunting of the crop plants results in loss of crop yield. The search continues for good selective herbicides.

Previous attempts are described to overcome this problem. The treatment of the crop seed with certain "hormonal" antagonistic agents to planting is described, see U.S. Pat. Nos. 3,131,509 and 3,564,768. The protective agents, as well as the herbicide, in these prior processes are largely specific to certain cultivated plant species or in the nature of the antagonistic agents. The prior antagonistic agents have not been notably successful. U.S. Pat. Nos. 4,021,224, 4,124,376, 4,137,070 and 3,989,503 relate to herbicide-antidote systems differing from previously cited patents. The aforementioned patents specifically exemplify and describe the treatment of seeds and soil treatment employing compounds of different chemical classes, not suggestive of the present invention.

DESCRIPTION OF THE INVENTION

It has been discovered that cultivated crop plants can be protected by guanidinyl-containing compounds against injury from thiolcarbamate-type herbicides, substituted p-toluidine derivative-type herbicides and the like, and said injury can be decreased when the herbicides, each alone or in mixtures or in combination with other compounds, are applied in a variety of ways. Further, as an alternative effect, the tolerance of the crop plants to these herbicides can be substantially increased by adding to the soil an antidote compound of the type—N-substituted guanidinyl.

Therefore, the present invention includes a two-part herbicide system consisting essentially of a first-part of one or more herbicides heretofore mentioned, and a second-part of an effective amount of an antidote compound therefore, said antidote compounds corresponding to the following formula

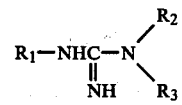

in which $R_1$ is halo substituted phenyl, particularly chlorophenyl, and $R_2$ and $R_3$ are individually selected from alkyl $C_1$–$C_4$ and alkenyl $C_3$–$C_4$.

The term "alkyl" includes straight chain, branched chain and cyclic substituents of this group having 1 to 4 carbon atoms, inclusive, for example, methyl, ethyl, n-propyl, iso-propyl, n-butyl, isobutyl, tert-butyl, cyclopropyl, cyclobutyl, cyclohexyl and the like. Alkenyl includes substituents of this group having 3–4 carbon atoms, inclusive, for example—allyl, butenyl-2, and the like.

The term "halo" includes those substituents such as chloro, bromo, iodo and fluoro as mono, di, tri or tetra substituents and combinations thereof.

By thiolcarbamate herbicides the present invention includes compounds of the formula

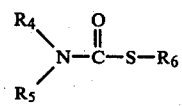

in which $R_4$ is selected from the group consisting of alkyl 1 to 6 carbon atoms and alkenyl 2 to 6 carbon atoms;

$R_5$ is selected from the group consisting of alkyl 1 to 6 carbon atoms, alkenyl 2 to 6 carbon atoms, cyclohexyl, phenyl and benzyl; or $R_4$ and $R_5$ taken together with the nitrogen atom to which they are attached form an alkylene ring substituted and unsubstituted 2 to 9 carbon atoms; and $R_6$ is selected from the group consisting of alkyl 1 to 6 carbon atoms, haloalkyl 1 to 6 carbon atoms, alkenylene ring 5 to 10 carbon atoms, phenyl, subsituted phenyl, benzyl and substituted benzyl.

By way of examplification, active thiolcarbamate herbicides employed in the present invention may include the following: S-ethyl N,N-dipropyl thiolcarbamate, S-ethyl N,N-diisobutyl thiolcarbamate, S-propyl N,N-dipropyl thiolcarbamate, S-2,3,3-trichloroallyl N,N-diisopropyl thiolcarbamate, S-ethyl N-cyclohexyl N-ethyl thiolcarbamate, S-ethyl hexahydro-1H-azepine-1-carbothioate, S-4-chlorobenzyl N,N-diethyl thiolcarbamate and combinations thereof.

By p-toluidine derivative type herbicides the present invention includes compounds such as α,α, α-trifluro-2,6-dinitro-N,N-dipropyl-p-toluidine (trifluralin) and other compounds as described in U.S. Pat. No. 3,257,190.

In general, the active antidote compounds of the persent invention can be prepared by the following methods.

The compounds of the present invention and their preparation are more particularly illustrated by the following examples. Following the examples of preparation is a table of compounds which are prepared according to the procedures described herein. Compound numbers have been assigned to them and are used for identification throughout the balance of the specification.

EXAMPLE

Preparation of 1,p-Chlorophenyl 3,3-diallyl guanidine.

p-Chloroaniline hydrochloride (4.1 grams, 0.025 mole) in 20 milliliters (ml) of ethanol with 3.05 grams (g) (0.025 mole) diallylcyanamide was refluxed for four hours. After cooling, the solvent was evaporated. There was obtained 7.0 g of the title compound, a semi-solid having the formula

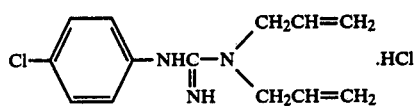

The structure was confirmed by infrared spectroscopy.

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. Within the present invention the prevention of injury to a desired crop species in the presence of a specific compound or combination may be achieved. The beneficial plant species which can be protected by this method is not intended to be limited by the specific crops employed in the examples.

The herbicidal compounds employed in the utility of this invention are active herbicides of a general type. That is, the members of the classes are herbicidally effective against a wide range of plant species with little or no discrimination between desirable and undesirable species. The method of controlling vegetation comprises applying an herbicidally effective amount of the herein described herbicidal compounds to the area or plant locus where control is desired.

An herbicide as used herein means a compound which adversely controls or modifies the growth of vegetation or plants. Such controlling or modifying effects include all deviations from natural development; for example, killing, retardation, defoliation, desiccation, regulation, stunting, tillering, stimulation, dwarfing and the like. By "plants" it is meant germinant seeds, emerging seedlings, and established vegetation, including the roots and above-ground portions.

The terms herbicide antidote or antidotal amount is meant to describe the effect which tends to counteract the normal injurious herbicidal response that the herbicide might otherwise produce. Whether it is to be termed a remedy, interferant, protectant, or the like, will depend upon the exact mode of action. The mode of action is varied, but the effect, which is desirable, is the result of the method of treating the seed, soil or furrow in which a crop is planted. Hitherto, there have been no systems employing the antidote of the present invention which have been for this purpose.

As alternative modes of action, the compounds of this invention may interfere with the normal herbicidal action of the thiolcarbamate-type thiolcarbamate sulfoxide-type or p-toluidine-type or other herbicides to render them selective in their action. The observation noted with the presence of the herein described antidote is a decrease in phytotoxicity with respect to various crops. The phytotoxicity is otherwise observed when various thiolcarbamates or p-toluidine-type herbicides are used for weed control. Whichever mode of action is present, the corresponding beneficial and desirable effect is the continued herbicidal effect of the thiolcarbamate or p-toluidine against weed species present with the crop, with the accompanying selective decreased herbicidal effect on desired crop species. This advantage and utility will become more apparent hereinafter.

Evaluation and Testing Procedure

Stock solutions of the herbicides were prepared by diluting the requisite amount of each herbicide in water or water and acetone. The solution compositions and application rates and methods are summarized in Table I.

Test Procedures and Results

TABLE I

| | Herbicide Stock Solution | | | | |
|---|---|---|---|---|---|
| | Composition | | | | |
| | Herbi-cide (mg) | Water or Acetone (ml) | Application | | |
| Herbicide Name | | | ml/flat | lb/acre | Method[1] |
| VERNAM ® S—propyl N,N—di-propyl thiolcarbamate | 413 2730 | 400 400 | 4 4 | 0.75 5.00 | PPI PPI |
| TREFLAN ® α,α,α-trifluoro-2,6-dinitro-N,N—di-propyl-p-toluidine | 80 | 100 | 5 | 1.0 | PPI |

[1]Method
PPI = Pre-plant incorporation

Stock solutions of each antidote compound were prepared at the desired concentration by diluting the requisite amounts of each antidote in acetone. The compositions and rates for each method of application are summarized in Table II.

TABLE II

| Antidote Stock Solutions | | | | |
|---|---|---|---|---|
| Antidote: Chlorophenyl diallyl guanidine.HCl | | | | |
| Composition | | Application | | |
| Antidote (mg) | Acetone (ml) | ml/flat | lb/acre | Method* |
| 95 STOCK A | 15 | 1.5 | 5.0 | IF |
| 100 | 10 | 2.0 | 5.0 | PPI |
| 20 | 50 | 5.0 | 0.5 | PPI |

*IF = In-furrow surface application
PPI = Pre-plant incorporation of herbicide and antidote as a tank mix All of the soil used in the tests described herein was loamy sand soil treated with 50 parts per million (ppm) each of a commercially available fungicide, cis-N[tri-chloromethyl)-thiol]-4-cyclohexene-1,2-dicarboximide, and 18-18-18 fertilizer, which contains 18% by weight equivalent each of nitrogen, phosphorus pentoxide, and potassium oxide.

As indicated in the tables, herbicides were applied to the soil by pre-plant incorporation (PPI) either alone or with the antidote as a tank mix. The antidote compounds were applied by PPI, pre-emergence surface (PES), seed treatment (ST), and in-furrow (IF) methods of application.

For in-furrow antidote applications, a one pint (473 cubic centimeter) sample of soil from each planting flat was removed and retained. After leveling and furrowing the soil, seeds of the crop or weed species were planted ½ inch (1.27 centimeter). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

For the pre-plant incorporation method the herbicide and the antidote of each test group were incorporated into the soil either each alone or together as a tank mix using a five gallon rotary mixer.

All flats were placed on greenhouse benches where temperature was maintained between 70° and 90° F. (21° to about 32° C.). The flats were watered be sprinkling as needed to assure good plant growth.

Control flats contained crops treated with herbicides only at the various rates and method of application.

Injury ratings were taken four weeks after application of the antidote. The effectiveness of the antidote was determined by visual comparison of injuries to crops and weeds in the control and test flats to those in untreated flats.

The treated crops initially screened for diminution of herbicidal injury were wheat (WH), rice (RC), and corn. Those compounds which showed substantial crop injury reduction were further tested at reduced rates. The herbicides and antidote compositions were then screened on at least one weed species. The weed species used for test control included watergrass (WG) (*Echinochloa crusgalli*), foxtail (FT) (*Setaria viridis*), wild oats (WO) (*Avena fatua*), mustard (MD) (*Brassica juncea*) and signalgrass (SG) (*Brachiaria platyphylla*).

KEY TO TABLE III

Antidotes

Compound numbers in this table correspond to the numbers and their chemical description in Table I.
Application:
- IF = In-furrow surface
- PPI-TM = Pre-plant incorporated of herbicide and antidote as a tank mix
- PPI = Pre-plant incorporatior of herbicide or antidote as indicated Rates are shown in pounds per acre based on the surface area of the flat.
Reported result=Treated/untreated (T/U).

TABLE III

| Antidote Rate & Method | Herbicide Rate & Method | Crop | Result |
| --- | --- | --- | --- |
| 5 PPI | ¾ PPI VERNAM | RC | 40/60 |
| 5 IF | 5 PPI VERNAM | CN | 0/70 |
| 5 IF | 1 PPI TREFLAN | WH | 70/95 |
|  |  | RC | 70/99 |

The antidote compounds and compositions of the present invention can be used in any convenient form. Thus, the antidote compounds can be formulated into emulsifiable liquids, emulsifiable concentrates, liquid, wettable powder, powders, granular or any other convenient form. In its preferred form, an herbicidal antidote compound in a non-phytotoxic quantity with respect to the crop is admixed with a selected herbicide and incorporated into the soil prior to or after planting the seed. It is to be understood, however, that the herbicides can be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not effect the herbicidal activity of the herbicides except to render the activity selective with respect to beneficial crops.

The amount of antidote compound present can range between about 0.01 to about 30 parts by weight of antidote compound described herein per each part by weight of herbicide. The exact amount of antidote compound will usually be determined on economic ratios for the most effective amount usable. It is understood that a non-phytotoxic quantity of antidote compound with respect to a particular crop will be employed in the herbicidal compositions described herein.

Formulations

The compounds and compositions can be formulated in the same manner in which herbicides are generally formulated. The object of the formulation is to apply the compounds and compositions to the locus where control is desired by a conventional method. The "locus" may include soil, seeds, seedlings, and vegetation.

The active herbicidal ingredient of a formulation will generally be such that its application rate will be within the range of 0.01 to 50 lb/A (0.0112 to 56 k/ha). The antidote compound which may be formulated separately or together with the herbicide will generally comprise about 0.01 to about 30 parts by weight of the herbicide.

Formulations will generally contain several additives. Among these are some inert ingredients, diluent carriers, organic solvents, water, oil and water, water in oil emulsions, carriers of dusts and granules, and surface active wetting, dispersing, and emulsifying agents.

Fertilizers, e.g., ammonium nitrate, urea and superphosphate, may also be included.

Aids to rooting and growth, e.g., compost, manure, humus, sand, etc., may likewise be included.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth, and pyrophyllite. Anti-caking and anti-static agents can be added, if desired. The composition generally contains up to 50% of active ingredient. Dusts, like liquid compositions, can be applied by spraying from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg,

*Pesticide Formulations*, (Marcel Dekker, Inc., N.Y., (1973)) at pages 79–84.

Granules comprise the herbicidal composition impregnated on a particulate inert carrier having a particle size of about 1 to 2 millimeters in diameter. The granules can be made by spraying a solution of the active ingredient in a volatile solvent onto the granule carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging, or mixing.

What is claimed is:

1. The method of protecting grain crops from injury due to at least one herbicide selected from S-propyl N,N-dipropyl thiolcarbamate and $\alpha,\alpha,\alpha$-trifluoro-2,6-dinitro-N,N-dipropyl-p-toluidine, comprising pre-plant incorporation in the soil in which said crop is to be planted, a non-phytotoxic antidotally effective amount of a compound corresponding to the formula $$R_1-NH-\underset{\underset{NH}{|}}{C}-N\diagup^{R_2}_{R_3} \cdot HCl$$

wherein $R_1$ is chloro substituted phenyl, $R_2$ and $R_3$ are individually selected from alkenyl $C_3$–$C_4$.

2. The method according to claim 1 in which $R_1$ is p-chlorophenyl.

3. The method according to claim 2 in which $R_2$ is allyl and $R_3$ is allyl.

4. The method of protecting grain crops from injury due to at least one herbicide selected from S-propyl N,N-dipropyl thiolcarbamate and $\alpha,\alpha,\alpha$-trifluoro-2,6-dinitro-N,N-dipropyl-p-toluidine, comprising applying infurrow to the seed and soil in which said crop is to be planted, a non-phytotoxic antidotally effective amount of a compound corresponding to the formula $$R_1-NH-\underset{\underset{NH}{|}}{C}-N\diagup^{R_2}_{R_3} \cdot HCl$$

wherein $R_1$ is chloro substituted phenyl, $R_2$ and $R_3$ are individually selected from alkenyl $C_3$–$C_4$.

5. The method according to claim 4 in which $R_1$ is p-chlorophenyl.

6. The method according to claim 4 in which $R_2$ is allyl and $R_3$ is allyl.

7. A herbicidal composition comprising at least one herbicide selected from S-propyl N,N-dipropyl thiolcarbamate and $\alpha,\alpha,\alpha$-trifluoro-2,6-dinitro-N,N-dipropyl-p-toluidine and an antidotally effective amount of a compound corresponding to the formula $$R_1-NH-\underset{\underset{NH}{|}}{C}-N\diagup^{R_2}_{R_3} \cdot HCl$$

wherein $R_1$ is chloro substituted phenyl and $R_2$ and $R_3$ are individually selected from alkenyl $C_3$–$C_4$.

8. The herbicidal composition according to claim 7 in which $R_1$ is p-chlorophenyl.

9. The method according to claim 8 in which $R_2$ is allyl and $R_2$ is allyl.

10. The method of decreasing injury to grain crops, said injury due to at least one herbicide of the following types: S-propyl N,N-dipropyl thiolcarbamate and $\alpha,\alpha,\alpha$-trifluoro-2,6-dinitro-N,N-dipropyl-p-toluidine comprising application to the soil in which said crop is planted and grown, a non-phytotoxic antidotally effective amount of an antidote compound corresponding to the formula $$R_1-NH-\underset{\underset{NH}{|}}{C}-N\diagup^{R_2}_{R_3} \cdot HCl$$

wherein $R_1$ is chloro substituted phenyl and $R_2$ and $R_3$ are individually selected from alkenyl $C_3$–$C_4$.

11. The method of claim 10 in which $R_1$ is p-chlorophenyl.

12. The method of claim 11 in which $R_2$ is allyl and $R_3$ is allyl.

* * * * *

UNITED STATES PATENT AND TRADEMARK OFFICE
CERTIFICATE OF CORRECTION

PATENT NO. : 4,468,246
DATED : August 28, 1984
INVENTOR(S) : Ferenc M. Pallos

It is certified that error appears in the above-identified patent and that said Letters Patent is hereby corrected as shown below:

In Column 6, line 33, ..."of 0:01 to..." should read ..."0.01"...

In Column 8, line 18, Claim 6, ..."to claim 4"... should read
..."to claim 5"...

In Column 8, line 36, Claim 9, "allyl and $R_2$ is allyl." should read
"allyl and $R_3$ is allyl."

Signed and Sealed this

Fourteenth Day of October, 1986

[SEAL]

Attest:

DONALD J. QUIGG

*Attesting Officer*  *Commissioner of Patents and Trademarks*